United States Patent
Kramer et al.

(10) Patent No.: US 6,303,823 B2
(45) Date of Patent: Oct. 16, 2001

(54) PROCESS FOR PREPARING KETONES, IN PARTICULAR 6-METHYLHEPTAN-2-ONE

(75) Inventors: Andreas Kramer, Bad Dürkheim; Christian Knoll, Neuhofen; Johann-Peter Melder, Böhl-Iggelheim; Wolfgang Siegel, Limburgerhof; Gerd Kaibel, Lampertheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/729,459

(22) Filed: Dec. 5, 2000

(30) Foreign Application Priority Data

Dec. 7, 1999 (DE) ................................................ 199 59 053

(51) Int. Cl.$^7$ .................................................. C07C 45/73
(52) U.S. Cl. .......................... 568/313; 568/315; 568/345; 568/347; 568/390; 568/391; 568/392
(58) Field of Search .................... 568/313, 315, 568/345, 347, 390, 391, 392

(56) References Cited

U.S. PATENT DOCUMENTS

| 4,146,581 | 3/1979 | Nissen et al. ......... 260/586 |
| 4,212,825 | * 7/1980 | Nissen et al. . |
| 4,408,079 | 10/1983 | Merger et al. ......... 568/463 |
| 4,496,770 | 1/1985 | Duembgen et al. ......... 568/463 |
| 5,004,839 | * 4/1991 | Pugach et al. . |
| 5,214,151 | * 5/1993 | Nakajima et al. . |
| 5,840,992 | * 11/1998 | Kido et al. . |

FOREIGN PATENT DOCUMENTS

| 26 15 308 | 10/1977 | (DE) . |
| 429 603 | 6/1991 | (EP) . |
| 058 927 | 9/1992 | (EP) . |
| 765 853 | 4/1997 | (EP) . |
| 771 782 | 5/1997 | (EP) . |
| 816 321 | 1/1998 | (EP) . |

OTHER PUBLICATIONS

Tigges et al. "Ferd Tiemann: Uber das Methyl–2–hepten–4–on–6 und die Synthese einer aliphatischen Isogeraniumsäure" Berichte vol. 33 (1900) pp. 559–566.
Etter "Neue Siynthesen der K öniginnensubstanz under 9–hydroxy–2$^{trans}$–Decensäure–(1)" Ann. vol. 658 (1962) pp. 91–99.
Bojikoba et al. "O МЕХАНИЗМЕ КОНДЕНСАЦИИ ЕНАМИНОВ С АЛЬДЕГИДАМИ" Dokl. Akad. Nauk SSSR vol. 149 (1963) pp. 94–96.
Engels et al. "Aledehydaddition an Enamine" Chem Ber. vol. 95 (1962) pp. 1495–1504.
Methoden der organischen Chemie, vol. 7/2b, 4th edition (1979) pp. 1452.
Methoden der organischen Chemie, vol. 7/1, 4th edition (1979) p. 87.

\* cited by examiner

*Primary Examiner*—Johann Richter
*Assistant Examiner*—Sikarl A. Witherspoon
(74) *Attorney, Agent, or Firm*—Keil & Weinkauf

(57) ABSTRACT

A process for preparing ketones by so-called "crossed aldol condensation" of a ketone with an aldehyde in the presence of a catalyst system consisting of approximately equimolar amounts of a secondary amine and of a carboxylic acid containing at least 2 C atoms, to form an α,β-unsaturated ketone, and, where appropriate, subsequent catalytic hydrogenation.

The process is used in particular for preparing 6-methyl-3-hepten-2-one by reacting acetone with isovaleraldehyde, and for preparing its hydrogenation product, 6-methylheptan-2-one, which is an important precursor for numerous active substances, in particular for preparing lipid-soluble vitamins such as vitamin E.

10 Claims, No Drawings

PROCESS FOR PREPARING KETONES, IN PARTICULAR 6-METHYLHEPTAN-2-ONE

The invention relates to a process for preparing ketones by a so-called "crossed aldol condensation" of a ketone with an aldehyde in the presence of a catalyst system consisting of approximately equimolar amounts of a secondary amine and a carboxylic acid, to form an $\alpha,\beta$-unsaturated ketone and, where appropriate subsequent catalytic hydrogenation.

The process is used in particular for preparing 6-methyl-3-hepten-2-one by reacting acetone with isovaleraldehyde, or for preparing the product of the hydrogenation of 6-methyl-3-hepten-2-one, 6-methylheptan-2-one (MHA), which is important as a precursor for numerous active substances, in particular for preparing lipid-soluble vitamins such as vitamin E.

The use of the aldol reaction for assembling higher ketones or aldehydes is widely used in organic synthesis and is extensively documented in the scientific literature. A review concerning this is provided inter alia by the work Houben-Weyl, *Methoden der organischen Chemie,* Volume 7/1, 4th edition, 1979, pages 77 et seq. and Volume 7/2b pages 1449 et seq.

Besides acid-catalyzed variants, aldol condensation methods with base catalysis are known, employing in many cases the hydroxides of the alkali metals and alkaline earth metals or else basic ion exchangers (cf. literature cited above).

The use of amines as catalyst for the aldol condensation has also been previously described in the literature (cf. Houben-Weyl, *Methoden der organischen Chemie,* Volume 7/1, 4th edition, 1979, pages 87 et seq. and Volume 7/2b, pages 1452 et seq.).

A disadvantage of the aldol condensation is, especially when the aldol condensation is carried out, for example, between a ketone and an aldehyde (i.e. a so-called "crossed aldol condensation"), that the selectivity is unsatisfactory; this is because the reactants in this case frequently undergo self-reaction to a large extent. This problem can in many cases be solved by specific preparation of an enamine of one of the reactants and further reaction thereof, as described, for example, by H. D. Engels et al. in Chem. Ber. 95 (1962), pages 1495–1504, or in the reference Dokl. Akad. Nauk SSSR, 149 (1963), page 94. However, increasing the selectivity in this way is at the expense of the need for another synthesis stage, including the appropriate work-up operations.

Although this process variant can be carried out without separate isolation of the enamine in the presence of an acid, according to the results of K. Eiter in Ann. 658 (1962), pages 91–99, the yields of this are only poor if both reactants are able to form an enamine.

Accordingly, the patents U.S. Pat. No. 5,214,151 and EP 0 771 780 have also described and claimed only aldol condensation of acetone with aromatic aldehydes, i.e. aldehydes unable to form enamines, in the presence of a secondary amine.

A complex catalyst system consisting of a secondary amine, a halogen acid and a carboxylic acid is claimed in the process disclosed in EP 0 429 603 B1 for addition of formaldehyde, in particular paraformaldehyde, onto ketones.

The preparation of 6-methyl-3-hepten-2-one by an aldol condensation of acetone with isovaleraldehyde in the presence of aqueous sodium hydroxide solution in relatively good yield has also been known for a long time (cf. Berichte 33 (1900), pages 559–566, in particular page 561).

One possibility for direct industrial preparation of MHA and similar ketones was offered, for example, by the process disclosed in DE 26 15 308, in which an aliphatic ketone, preferably acetone, can be reacted with an aliphatic aldehyde, for example isovaleraldehyde, in the presence of hydrogen and of a catalyst system which catalyzes both the condensation of ketone and aldehyde and the subsequent hydrogenation, at temperatures of 80–280° C. The process is advantageously carried out continuously over a fixed bed catalyst. When carried out industrially, yields of more than 80% of theory can be isolated. The disadvantage of this process is, at the most, that relatively high temperatures must be used, leading to the risk of unwanted byproducts due to overhydrogenation.

EP 765 853 A1 describes a process for preparing MHA by aldol condensation in which acetone and isovaleraldehyde are condensed in the presence of a basic compound to give 4-hydroxy-6-methylheptan-2-one, and the resulting condensation product is hydrogenated under dehydrating conditions. The particular disadvantage of the process is that the condensation in the first process step proceeds only with inadequate yields. Thus, as proved by the examples, the yields determined by gas chromatography after the condensation for 4-hydroxy-6-methylheptan-2-one and the directly formed 6-methyl-3-hepten-6-one total only 76.1% in Example 1 and 80.6% in Example 2. Since there is also loss of required product through elaborate work-up steps and, as proved by the examples, the maximum yields achieved in the subsequent hydrogenation under dehydrating conditions are only 92%, the maximum yields which can be achieved in this process are, despite the elaborate process management, only 74%, which is inadequate for an industrial process.

EP 816 321 A1 discloses a process for preparing 6-methyl-3-hepten-2-one by crossed aldol condensation in which isovaleraldehyde and aqueous alkali containing a basic substance are introduced at elevated temperature continuously into excess acetone. The disadvantage of this process is that the yield of 6-methyl-3-hepten-2-one determined by gas chromatographic analysis is 66% of theory which is absolutely unsatisfactory.

EP 816 321 A1 further discloses in claim 11 a process for preparing 6-methylheptan-2-one or its homologs in which hydrogen, acetone and an aldehyde are said to be reacted in the presence of aqueous alkali containing a basic substance, and of a conventional hydrogenation catalyst. The disadvantage of this process is that the selectivities determined by gas chromatography for 6-methylheptan-2-one in most of the examples of this process are less than 70% of theory. In the single more advantageous example, the selectivity after work-up is only about 82%.

It is an object of the present invention to develop a process for the industrial preparation of ketones, in particular 6-methyl-3-hepten-2-one, by crossed aldol condensation of acetone with an aliphatic aldehyde, in particular with isovaleraldehyde, and, where appropriate, subsequent hydrogenation to 6-methylheptan-2-one, which permits the ketone to be prepared on the industrial scale even without use of very high temperatures and without elaborate work-up steps during the ketone synthesis and with very good selectivities.

We have found that this object is achieved because it is possible even with ketones and aldehydes which are capable of self-condensation under the conditions of an aldol condensation, and both of which are able to form an enamine, such as acetone and isovaleraldehyde, to carry out a crossed aldol condensation between the aldehyde and the ketone in good yields and with very good selectivities when the reaction is carried out in the presence of a catalyst system which consists of a specific secondary amine such as dimethylamine or pyrrolidine, and of a carboxylic acid containing at least 2 C atoms, in particular acetic acid, adipic acid or phthalic acid. The β-hydroxy ketone initially produced in aldol condensations is in this case found only in very small amounts in the discharge from the reaction.

The novel process is advantageously carried out in such a way that initially excess ketone is mixed with the secondary amine and the carboxylic acid in the presence of water, and heated, and then the aldehyde, for example isovaleraldehyde, is slowly added. This management of the reaction makes it possible to prepare α,β-unsaturated ketones with selectivities of more than 92%. The conversion based on the aldehyde, which is employed in less than the stoichiometric amount, is quantitative in this case.

The invention accordingly relates to a process for preparing α,β-unsaturated ketones of the formula I

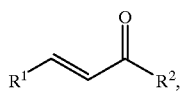
(I)

in which $R^1$ is an unbranched or branched cyclic or acyclic saturated or unsaturated aliphatic radical having 4 to 20 C atoms, and $R^2$ is a branched or unbranched cyclic or acyclic saturated or unsaturated aliphatic radical having 1 to 10 C atoms, by reacting a ketone of the formula II

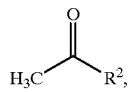
(II)

with an aldehyde of the formula III

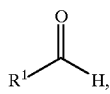
(III)

in which $R^1$ has the abovementioned meaning, wherein the ketone is heated under reflux in the presence of a catalyst system consisting of dimethylamine or pyrrolidine and a carboxylic acid containing at least 2 C atoms, preferably a carboxylic acid containing 2 to 10 C atoms, in particular acetic acid, adipic acid or phthalic acid, and the aldehyde of the formula III is slowly added to this mixture.

Although EP 0 058 927 B1 and EP 0 092 097 B1 have disclosed processes for preparing α-alkylacroleins by reacting alkanals with formaldehyde and secondary amines in the presence of carboxylic acids or dicarboxylic acids, in these processes, which are based on the Mannich reaction, the formaldehyde is activated as acceptor component by means of the amine as shown in Scheme 1 below (cf. Organikum, 16th edition (1986), pages 466 et seq.).

Scheme 1

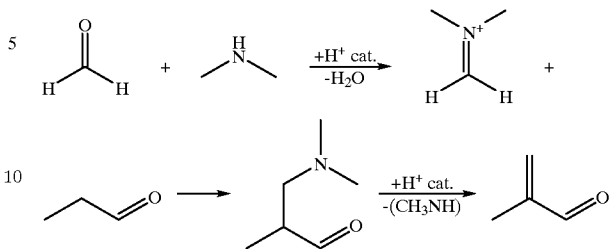

The process described herein contrasts with this in that, as shown in Scheme 2, the donor component is activated by formation of an intermediate enamine.

Scheme 2

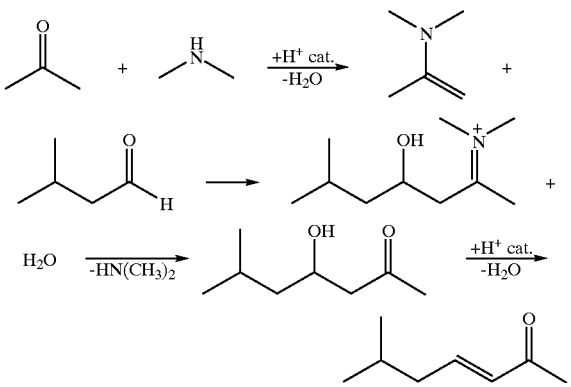

It is important for achieving good conversions and good selectivities that the ketone, in particular the acetone, is used in a molar excess in relation to the aldehyde of the formula III. Advantageous amounts of ketone have proven to be at least 2 mol per mole of the aldehyde of the formula III, preferably about 4 to 8 mol, in particular about 5 mol, per mole of the aldehyde of the formula III.

The process of the invention proceeds particularly advantageously when the dimethylamine or the pyrrolidine and the carboxylic acid are employed in approximately equimolar amounts in the catalyst system, and this catalyst system is used in amounts of about 0.5 to 10 mol %, preferably 7 to 8 mol %, in particular about 7.5 mol %, based on the aldehyde of the formula III, which is generally employed in less than the stoichiometric amount.

Particularly good selectivities for the unsaturated ketone are achieved with the aid of the process of the invention on use of a catalyst system which consists of dimethylamine and acetic acid.

It is advantageous to use the dimethylamine or the pyrrolidine in the form of an aqueous solution.

To prepare the corresponding saturated ketone, in particular 2-methylheptan-2-one, the reaction mixture obtained after the process of the invention and containing the unsaturated ketone of the formula I can, after removal of the aqueous phase which is formed and without further work-up, be hydrogenated in a manner known per se to the corresponding saturated ketone.

Ketones which may be mentioned as particularly suitable for the process of the invention are acetone, methyl ethyl ketone and cyclohexanone, and particularly suitable aldehydes which may be mentioned are propionaldehyde, butyraldehyde, valeraldehyde, isovaleraldehyde, citronellal, 3-(tert-butylphenyl)-2-methylpropanal, 3-(methylphenyl)-2-methylpropanal and 3-(methoxyphenyl)-2-methylpropanal, in particular isovaleraldehyde and citronellal.

Amines which may be mentioned as particularly suitable are secondary amines such as pyrrolidine and dimethylamine, in particular dimethylamine.

Carboxylic acids with 2 to 10 C atoms are suitable and preferred as carboxylic acid. It is immaterial in this connection whether an aliphatic or an aromatic carboxylic acid is used. It is also possible to use carboxylic acids containing 2 or more carboxyl groups, such as adipic acid or phthalic acid. It is particularly advantageous to use acetic acid, phthalic acid and adipic acid, especially acetic acid.

The reaction can be carried out under atmospheric pressure or under elevated pressures. However, atmospheric pressure is generally sufficient.

The temperature may be varied over a wide range between about −10 and 200° C. If, for example acetone is used as ketone component, the reaction is preferably carried out at the temperature at which the acetone in the mixture boils.

The process of the invention can be carried out both batchwise and semicontinuously or continuously.

The novel process is particularly suitable for preparing 6-methylheptan-2-one, in which case firstly acetone is reacted with isovaleraldehyde in the presence of a catalyst consisting of aqueous dimethylamine and acetic acid, and the reaction product which, after removal of the aqueous phase which is formed, consists essentially of 6-methyl-3-hepten-2-one (MHE), is hydrogenated with hydrogen over a hydrogenation catalyst in a manner known per se to give MHA.

As Example 15 shows, the discharge from the condensation, from which the aqueous phase which has formed has been removed, can be hydrogenated over a conventional hydrogenation catalyst, such as a catalyst containing 5% by weight of Pd on activated carbon, at 3 to 20° C. and under a pressure of about 1 bar of hydrogen, that is to say under very mild hydrogenation conditions, with quantitative conversion.

Examples of usual hydrogenation catalysts which are suitable are catalysts which contain at least one element of group 8 to 10 of the Periodic Table, preferably Ni or Co, or else a noble metal such as Pt, Pd, Rh, Ru, Ir, Au or Ag, in particular Pd. The hydrogenation catalysts can be employed in the form of the metals or oxides on inert support materials such as carbon, $SiO_2$, $TiO_2$, $ZrO_2$ or $Al_2O_3$ or else in unsupported form, as is the case, for example, on use of Raney nickel or Raney cobalt.

The hydrogenation can be carried out under conventional conditions under a gage pressure of 0.5 to 50 bar of hydrogen, preferably 1 to 10 bar, and at temperatures of 0 to 100° C., preferably 20 to 40° C.

The work-up can take place at the stage of the unsaturated ketone or after the hydrogenation by means of conventional methods, for example by distillation or crystallization.

MHA is an important precursor for preparing lipid-soluble vitamins such as vitamin E. A large number of synthetic methods exists in the scientific literature, as mentioned inter alia in EP 816 321. The disadvantage of these processes which should be mentioned is often the poor relation between selectivity and space-time yield.

It is possible by the process of the invention to prepare 6-MHA with selectivities of >92% based on the aldehyde, which is employed in less than the stoichiometric amount, in good space-time yields.

It is also possible to obtain with unexpectedly high selectivities 6,10-dimethylundeca-3,9-dien-2-one, which is suitable for preparing various active substances, and is therefore in demand, as well as 6-(tert-butylphenyl)-5-methylhexan-2-one.

A further possibility is to convert the ketones resulting from the condensation, depending on the nature of the catalyst employed and the chosen reaction conditions, into the corresponding alcohols.

Examples 1 to 6 and Comparative Examples 1* to 5*

General Test Procedure

The tests were carried out in a 250 ml stirred apparatus with fitted reflux condenser and dropping funnel by the following standard method:

General Process Procedure 113 g (1.95 mol) of acetone and the amount of catalyst stated in the table (stated in mol % based on the aldehyde) were heated to reflux with stirring in the stirred apparatus. Then 0.65 mol of isovaleraldehyde (IVA) was added dropwise to this boiling mixture over the course of 5 to 6 hours (h) under atmospheric pressure and, after completion of the dropwise addition, the reaction mixture was stirred for 1 h. The tests were analyzed by gas chromatography (GC) on the basis of the GC percentage areas (method: 50 m OV 1701, 25 μm, 50/10/240), counting acetone as solvent and not including it in the analysis. To calculate the conversion and selectivity, the total of the required products (RP) was formed from the reaction products 6-MHE, its unconjugated isomers and the β-hydroxy ketone (6-MHOL).

1) Influence of the Amine Used

The amine components tested for the catalyst system were dimethylamine (DMA), diethylamine (DEA), pyrrolidine (Pyrr), piperidine (Pip) and morpholine (Morph) in the presence of acetic acid. This was done by preparing the catalyst systems by dropwise addition of acetic acid to each of the amines in the form of a 40% by weight solution in water, with cooling. In Comparative Example 5*, diethanolamine (DIEA) and oxalic acid (oxal) were employed as catalyst. In Comparative Example 4*, only aqueous DMA solution was employed without acid. The results of the tests are summarized in Table 1.

TABLE 1

| Example or Comp. Example* | Acetone [molar ratio] | Catalyst system | Amount of catalyst [mol %] based on IVA | Reaction time [h] | Unconj. 6-MHE [GC % area] | 6-MHE [GC % area] | 6-MHOL [GC % area] | Total RP [GC % area] | Conversion [%] | Selectivity [%] |
|---|---|---|---|---|---|---|---|---|---|---|
| 1 | 3/1 | DMA/HOAc | 7.5 | 7 | 4.4 | 80.1 | 0.8 | 84.4 | 96.2 | 87.8 |
| 2 | 3/1 | Pyrr./HOAc | 7.5 | 7 | 4.6 | 58 | 1.8 | 62.0 | 100 | 62.5 |
| 3 | 3/1 | Pyrr./HOAc | 7.5 | 5.25 | 6.2 | 59.9 | 1.2 | 66.1 | 100 | 66.1 |
| 4 | 4/1 | Pyrr./HOAc | 3.75 | 6 | 6.0 | 62.3 | 1.7 | 68.2 | 100 | 68.2 |
| 5 | 4/1 | Pyrr./HOAc | 1.9 | 6 | 7.1 | 72.2 | 1.5 | 79.3 | 99.78 | 79.5 |
| 6 | 4/1 | DMA/HOAc | 3.75 | 6 | 2.6 | 58.1 | 0.7 | 60.7 | 82.4 | 73.6 |
| 1* | 4/1 | DME/HOAc | 7.5 | 6 | 3.0 | 30.4 | 1.8 | 33.4 | 61.5 | 54.3 |
| 2* | 4/1 | Morph./HOAc | 1.9 | 5.5 | 0.2 | 5.6 | 2.4 | 5.8 | 13.0 | 44.5 |
| 3* | 4/1 | Pip./HOAC | 1.9 | 5.5 | 0.4 | 12.1 | 0.7 | 12.6 | 27.22 | 46.1 |
| 4* | 3/1 | DMA | 7.5 | 5.5 | 2.1 | 60.3 | 1.6 | 64.0 | 96.0 | 66.7 |
| 5* | 3/1 | DIEA/oxal. | 7.5 | 5.5 | — | — | — | — | 9 | 0 |

The results in Table 1 show that with the dimethylamine/acetic acid catalyst system it is possible to achieve, with virtually complete conversion, the highest selectivities when the catalyst is employed in amounts of about 7.5 mol % in relation to the isovaleraldehyde IVA. All the other amine/carboxylic acid combinations afford less good selectivities or, as in the case of the diethanolamine/oxalic acid system, fail entirely.

2) Variation of the Brönstedt Acid

Examples 7 to 9 and Comparative Examples 6* to 19*

Dimethylamine was employed as base for these tests. The Brönstedt acids employed were, as organic acids, acetic acid, adipic acid, phthalic acid and oxalic acid, as well as the acidic ion exchangers Dowex 50 WX8, Lewatit SPC 112/H, and, as inorganic acids, Amberlist 15, Amberlite IR, Deloxan, β-zeolite GE 1494, montmorillonite KSF, $Al_2O_3$ and bentonite K-10. The amount of the heterogeneous acids was fixed at 0.5 g, and the amount of 40% strength aqueous DMA required for neutralization was determined in preliminary tests.

The soluble catalyst systems (DMA/adipic acid, DMA/phthalic acid and DMA/oxalic acid) were used, as stated above for the amine, in the ratio of 7.5 mol % based on the aldehyde IVA employed. The ratio of acetone to IVA was set at 3:1.

The results are shown in Table 2.

TABLE 2

| Example or Comp. Example* | Catalyst system DMA/acid | Amount of acid [g] | Unconj. 6-MHE [GC % area] | 6-MHE [GC % area] | 6-MHOL [GC % area] | Total RP [GC % area] | Conversion [%] | Selectivity [%] |
|---|---|---|---|---|---|---|---|---|
| 7 | HOAc | 2.72 | 4.4 | 80.1 | 0.8 | 84.4 | 96.2 | 87.8 |
| 6* | Dowex | 0.5 | 0.4 | 5.1 | 0.4 | 5.9 | 14.4 | 40.7 |
| 7* | Dowex | 0.7 | 0.2 | 1.7 | 0.2 | 2.1 | 6.5 | 28.1 |
| 8* | Lewatit | 0.5 | 0.0 | 3.7 | 0.0 | 3.7 | 13.3 | 30.8 |
| 9* | Amberlist | 0.5 | 0.0 | 2.9 | 0.0 | 2.9 | 13.3 | 27.4 |
| 10* | Amberlite | 0.5 | 0.0 | 7.4 | 0.0 | 7.4 | 21 | 36.7 |
| 11* | Deloxan | 0.5 | 0.0 | 8.9 | 0.0 | 8.9 | 23.9 | 37.2 |
| 12* | Zeolite | 0.5 | 0.7 | 14.6 | 0.2 | 15.5 | 27.4 | 56.4 |
| 13* | Montmorillonite | 0.5 | 1.6 | 4.9 | 0.1 | 6.6 | 14.4 | 45.7 |
| 8 | Phthalic acid | 4.0 | 6.05 | 72.9 | 0.6 | 78.9 | 97.8 | 80.7 |
| 9 | Adipic acid | 7.1 | 2.6 | 61.4 | 0.2 | 66.6 | 86 | 77.5 |
| 14* | Al2O3 | 0.5 | 0.5 | 10.4 | 0.6 | 11.5 | 34.1 | 33.7 |
| 15* | Phthalic acid** | 8.1 | 0.0 | 0.0 | 0.0 | 0.0 | 2.8 | 0.0 |
| 16* | Bentonite | 0.5 | 0.9 | 28.6 | 0.8 | 29.6 | 64.8 | 45.7 |
| 17* | Zeolite | 0.5 | 1.4 | 19.8 | 0.6 | 21.8 | 47.3 | 46.2 |
| 18* | Al2O3 | 0.5 | 0.4 | 8.9 | 0.5 | 9.8 | 25.3 | 36.7 |
| 19* | Oxalic acid | 3.0 | 0.0 | 11.6 | 0.0 | 11.6 | 18.3 | 63.4 |

**means: the test was carried out in the absence of a base

The results shown in Table 2 reveal the surprising distinct superiority of the water-soluble catalyst systems compared with the partially heterogeneous catalyst systems, with acetic acid proving to be the best acid component. Acetic acid was therefore also employed for the following tests. However, phthalic acid and adipic acid are also very suitable alternatives for the condensation step.

In Comparative Test 15* a failed attempt was made to carry out the condensation in the absence of an amine, i.e. only in the presence of phthalic acid.

Example 10 and Comparative Examples 20* to 23*

In each case, 70 g of acetone were mixed at room temperature (Rt) with the amount of DMA evident from Table 3 below, and the acid stated in Table 3, in the amount stated therein (equivalent to 7.5 mol % of catalyst system) in a stirred apparatus and heated with stirring. After the reflux temperature had been reached, 34.4 g of IVA dissolved in 46.5 g of acetone were added dropwise over the course of 5 h. The discharges from the reaction were analyzed by GC.

TABLE 3

| Example or Comparative Example* | Amount of dimethyl-amine | Amount of acid | IVA conversion | Yield of 6-MHE |
|---|---|---|---|---|
| 10 | 1.32 g | 1.8 g acetic acid | >99% | 84.2% |
| 20* | 1.32 g | 1.38 g formic acid | 21% | 13.0% |
| 21* | 1.32 g | 3.0 g phosphoric acid | 0% | 0% |
| 22* | 2.64 g | 3.0 g phosphoric acid | 35% | 15.6% |
| 23* | 3.96 g | 3.0 g phosphoric acid | 70% | 35.4% |

It is evident from Comparative Tests 20* to 23* that the selectivities for 6-MHE are considerably worse with formic acid or phosphoric acid as acids in the catalyst system than with acetic acid.

3) Determination of the Effect of Time, Water Content in the Catalyst System and the Acetone/IVA Ratio on the Selectivity Examples 11 to 14

The catalyst system employed was DMA/acetic acid in the standard method described above (7.5 mol % in each case), but with an acetone/IVA ratio of 5:1, using 40% of the acetone for previous dilution of the IVA. The results have been presented in Table 4.

The results presented in Table 4 show that it is possible by increasing the acetone/IVA ratio to 5/1 to increase the selectivity of the aldol condensation to more than 92%.

TABLE 4

| Example | Acetone/ IVA ratio | Amount of water in the catalyst system [%] | Reaction time [h] | Unconjugated 6-MHE [GC % area] | 6-MHE [GC % area] | 6-MHOL [GC % area] | Total RP [GC % area] | Conversion [%] | Selectivity [%] |
|---|---|---|---|---|---|---|---|---|---|
| 11 | 3/1 | 40 | 7<sup>1)</sup> | 4.4 | 80.1 | 0.8 | 84.4 | 96.2 | 87.8 |
| 12 | 5/1 | 40 | 5.5 | 4.4 | 87.1 | 0.6 | 92.1 | 99.9 | 92.2 |
| 13 | 5/1 | 40 | 10.5 | 5.9 | 86.4 | 0.1 | 92.3 | 100 | 92.3 |
| 14 | 5/1 | 68 | 5.5 | 5.0 | 86.7 | 0.3 | 92.0 | 100 | 92.0 |

4) Hydrogenation of the Crude Discharge

Example 15

100 g of the discharge from the reaction in Example 12 (see Table 4) were, after removal of the aqueous phase resulting in the condensation reaction and without further work-up, hydrogenated in the presence of 2 g of a hydrogenation catalyst containing 5% by weight of Pd on carbon at 20° C. and under a pressure of about 1 bar of hydrogen. Hydrogen uptake ceased after 2.5 h. GC analysis of the discharge from the hydrogenation confirmed the quantitative conversion of 6-MHE into the desired 6-methylheptanone. This test demonstrates that it is possible in principle to hydrogenate 6-MHE under very mild conditions with unexpectedly high selectivities to the saturated ketone.

Example 16

150 g of acetone were mixed at Rt with 1.32 g of dimethylamine and 1.8 g of acetic acid (equivalent to 7.5 mol % based on the catalyst system) in a stirred apparatus and heated with stirring. After the reflux temperature had been reached, 100 g of citronellal were added dropwise over the course of 5 h to the boiling reaction mixture. The discharges from the reaction were analyzed by GC. The conversion of citronellal was 84%, and the selectivity for 6,10-dimethylundeca-3,9-dien-2-one was 95% of theory.

We claim:

1. A process for preparing α,β-unsaturated ketones of the formula I

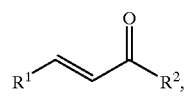

(I)

in which $R^1$ is a branched or unbranched cyclic or acyclic saturated or unsaturated aliphatic or araliphatic radical having 4 to 20 C atoms, and $R^2$ is a branched or unbranched cyclic or acyclic saturated or unsaturated aliphatic or araliphatic radical having 1 to 10 C atoms, by reacting a ketone of the formula II

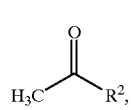

(II)

in which $R^2$ has the abovementioned meaning, with an aldehyde of the formula III

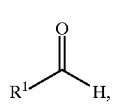

(III)

in which $R^1$ has the abovementioned meaning, wherein the ketone is heated under reflux in molar excess in the presence of a catalyst system consisting of dimethylamine or pyrrolidine and a carboxylic acid containing at least 2 C atoms, and the aldehyde of the formula III is slowly added to this mixture.

2. A process as claimed in claim 1, wherein the dimethylamine or the pyrrolidine and the carboxylic acid are employed in approximately equimolar amounts in the catalyst system.

3. A process as claimed in claim 1, wherein the catalyst system is used in amounts of about 5 to 10 mol %, based on the aldehyde of the formula III.

4. A process as claimed in claim 1, wherein the catalyst system is used in amounts of about 7 to 8 mol %, based on the aldehyde of the formula III.

5. A process as claimed in claim 1, wherein the catalyst system consists of dimethylamine or pyrrolidine and a carboxylic acid containing 2 to 10 C atoms.

6. A process as claimed in claim 1, wherein the catalyst system consists of dimethylamine and acetic acid.

7. A process as claimed in claim 1, wherein the dimethylamine or the pyrrolidine is used in the form of an aqueous solution.

8. A process as claimed in claim 1, wherein the unsaturated ketone of the formula I resulting after removal of the aqueous phase which is formed, and without further work-up, is hydrogenated in a manner known per se to the corresponding saturated ketone.

9. A process as claimed in claim 1, wherein the ketone is used in an at least 2-molar excess in relation to the aldehyde of the formula III.

10. A process as claimed in claim 1, wherein 6-methylheptan-2-one is prepared by reacting isovaleraldehyde with acetone in a 4.5- to 5.5-fold molar excess in the presence of a catalyst system consisting of approximately equimolar amounts of dimethylamine and acetic acid in amounts of about 6 to 8 mol %, based on the isovaleraldehyde, and the resulting 6-methyl-3-hepten-2-one is catalytically hydrogenated in a manner known per se.

* * * * *